United States Patent
Agassi et al.

(10) Patent No.: US 11,348,672 B2
(45) Date of Patent: May 31, 2022

(54) MEDICAL ORDER ENTRY INTEGRATION WITH AUTOMATED DISPENSING SYSTEMS

(71) Applicant: CERNER INNOVATION, INC., Kansas City, KS (US)

(72) Inventors: Natalee Agassi, Blue Bell, PA (US); Emin Agassi, Blue Bell, PA (US)

(73) Assignee: CERNER INNOVATION, INC., North Kansas City, MO (US)

(*) Notice: Subject to any disclaimer, the term of this patent is extended or adjusted under 35 U.S.C. 154(b) by 138 days.

(21) Appl. No.: 15/858,042

(22) Filed: Dec. 29, 2017

(65) Prior Publication Data
US 2019/0206540 A1    Jul. 4, 2019

(51) Int. Cl.
G16H 20/13     (2018.01)
G06Q 10/08     (2012.01)
G06Q 10/10     (2012.01)

(52) U.S. Cl.
CPC .......... *G16H 20/13* (2018.01); *G06Q 10/087* (2013.01); *G06Q 10/109* (2013.01)

(58) Field of Classification Search
CPC ........ G06Q 50/22; G06Q 50/24; G06Q 40/08; G06Q 10/08; G06Q 10/087; G06Q 10/00
USPC .......................................................... 705/2
See application file for complete search history.

(56) References Cited

U.S. PATENT DOCUMENTS

| | | | |
|---|---|---|---|
| 4,384,201 A | 5/1983 | Carroll et al. | |
| 4,717,042 A | 1/1988 | McLaughlin | |
| 4,785,969 A | 11/1988 | McLaughlin | |
| 4,953,745 A | 9/1990 | Rowlett, Jr. | |
| 5,014,875 A | 5/1991 | McLaughlin et al. | |
| 5,190,185 A | 3/1993 | Blechl | |
| 5,377,864 A | 1/1995 | Blechl et al. | |
| 5,392,951 A | 2/1995 | Gardner et al. | |
| D357,581 S | 4/1995 | Rogers et al. | |

(Continued)

FOREIGN PATENT DOCUMENTS

WO    WO-2013157851 A1 * 10/2013 ............. G07F 9/001

OTHER PUBLICATIONS

Pulver, Gerald E; An exploration of ambulatory prescription and community pharmacy fulfillment data for improvement of electronic processes; University of Colorado Denver, Anschutz Medical Campus. ProQuest Dissertations Publishing, 2015. 3708203 (Year: 2015).*

(Continued)

*Primary Examiner* — Hiep V Nguyen
(74) *Attorney, Agent, or Firm* — Shook, Hardy & Bacon L.L.P.

(57) ABSTRACT

Systems and methods are provided for facilitating the dispensing of a medication from a dispensing station by using information from a dispensing event to instruct the dispensing station to dispense the medication. A dispensing event is received, which is associated with an order for an individual. The dispensing event is processed, which may include mapping the ordered medication to a table having one or more medications and available dosages, identifying corresponding medications to the ordered medication, selecting one of the corresponding medications, and computing a quantity of the selected medication for administration to the patient. The dispensing station is then instructed to dispense the computed quantity of the corresponding medication.

18 Claims, 7 Drawing Sheets

(56) References Cited

U.S. PATENT DOCUMENTS

| | | | |
|---|---|---|---|
| 5,405,048 A | 4/1995 | Rogers et al. |
| 5,409,117 A | 4/1995 | Meador |
| 5,411,065 A | 5/1995 | Meador et al. |
| 5,445,294 A | 8/1995 | Gardner et al. |
| 5,460,294 A | 10/1995 | Williams |
| 5,480,062 A | 1/1996 | Rogers et al. |
| 5,520,450 A | 5/1996 | Colson, Jr. et al. |
| 5,549,141 A | 8/1996 | Meador et al. |
| 5,641,093 A | 6/1997 | Dolin et al. |
| 5,661,978 A | 9/1997 | Holmes et al. |
| 5,716,114 A | 2/1998 | Holmes et al. |
| 5,745,366 A | 4/1998 | Higham et al. |
| 5,805,455 A | 9/1998 | Lipps |
| 5,805,456 A | 9/1998 | Higham et al. |
| 5,842,976 A | 12/1998 | Williamson |
| 5,883,806 A | 3/1999 | Meador et al. |
| 5,905,653 A | 5/1999 | Higham et al. |
| 5,927,540 A | 7/1999 | Godlewski |
| 5,940,306 A | 8/1999 | Gardner |
| 6,011,999 A | 1/2000 | Holmes |
| 6,021,392 A | 2/2000 | Lester |
| 6,039,467 A | 3/2000 | Holmes |
| 6,065,819 A | 5/2000 | Holmes et al. |
| 6,068,156 A | 5/2000 | Liff et al. |
| 6,109,774 A | 8/2000 | Holmes et al. |
| 6,116,461 A | 9/2000 | Broadfield et al. |
| 6,151,536 A | 11/2000 | Arnold et al. |
| 6,175,954 B1 | 1/2001 | Nelson et al. |
| 6,272,394 B1 | 8/2001 | Lipps |
| 6,275,152 B1 | 8/2001 | Speas et al. |
| 6,338,007 B1 | 1/2002 | Broadfield et al. |
| 6,339,732 B1 | 1/2002 | Phoon et al. |
| 6,361,263 B1 | 3/2002 | Dewey et al. |
| 6,385,505 B1 | 5/2002 | Lipps |
| 6,499,270 B2 | 12/2002 | Peroni et al. |
| 6,609,047 B1 | 8/2003 | Lipps |
| 6,640,159 B2 | 10/2003 | Holmes et al. |
| 6,760,643 B2 | 7/2004 | Lipps |
| 7,146,247 B2 | 12/2006 | Kirsch et al. |
| 7,203,571 B2 | 4/2007 | Kirsch et al. |
| 2001/0002448 A1 | 5/2001 | Wilson et al. |
| 2001/0029405 A1 | 10/2001 | Lipps |
| 2001/0032025 A1 | 10/2001 | Lenz et al. |
| 2002/0095238 A1 | 7/2002 | Ahlin et al. |
| 2003/0078693 A1 | 4/2003 | Chavez et al. |
| 2004/0004419 A1 | 1/2004 | Godlewski |
| 2004/0026442 A1 | 2/2004 | Hutchinson |
| 2004/0040975 A1 | 3/2004 | Hunter et al. |
| 2004/0111179 A1 | 6/2004 | Broadfield et al. |
| 2004/0220697 A1 | 11/2004 | Chavez et al. |
| 2004/0225409 A1 | 11/2004 | Duncan et al. |
| 2005/0033606 A1* | 2/2005 | Miller .................. G06Q 50/22 705/2 |
| 2014/0214199 A1* | 7/2014 | Utech .................. G16H 40/20 700/236 |

OTHER PUBLICATIONS

Cardinal Health, Pyxis Products, www.pysix.com/products/index.asp website, published Jun. 3, 2004.

Medication Automation, Your total automated medication management system, www.pyxis.com/products/medhomes.asp website, published Jun. 3, 2004.

Pysix MedStation Rx 2000, Advanced profile-based automated medication dispensing system, www.pyxis.com/products/medstationrx2000.asp website, published Jun. 3, 2004.

* cited by examiner

MEDICAL ORDER ENTRY INTEGRATION WITH AUTOMATED DISPENSING SYSTEMS

BACKGROUND

Many hospitals include a hospital pharmacy department that is responsible for dispensing medications to individuals (e.g., patients) in various areas of the hospitals. In some hospitals, the medications are dispensed in a distributed environment with a central pharmacy (or multiple "central" pharmacies) and a number of medication dispensing apparatuses (e.g., medication dispensing cabinet) remotely situated in various locations throughout the hospital. The remotely-located medication dispensing apparatuses allow medications to be stored and dispensed closer to the location of patient care, which may provide a number of benefits, including simplifying and speeding up the process of clinicians obtaining medications for their patients.

The typical process of dispensing medications from medication dispensing apparatuses includes a number of steps, such as requiring identification of the clinician dispensing the medications, identification of the patient for which the medications are dispensed, medication interaction checking, allergy checking, duplicate checking, medication counting, and other pharmacy verification. These steps are typically required for a variety of reasons, including patient safety, controlling the dispensing of medications, and auditing purposes, to name a few. However, this process is slow, and typically requires a clinician to understand what is available in each dispensing apparatus, which medication to select from a dispensing apparatus, how much to dispense based on available dosage units for that medication and the ordered dosage, etc.

BRIEF SUMMARY

Embodiments of the present invention relate to methods and systems for facilitating the dispensing of a medication, where a dispensing event is used to perform functions to determine which medication to dispense, from which dispensing station the medication is to be dispensed, a dosage of that medication, an administration schedule, and the like. In embodiments, a central dispensing system communicates with multiple dispensing stations using a specialized event-based infrastructure configuration and various components. A clinician may manually and/or automatically prepare and input a dispensing event into a dispensing queue, where the system will retrieve the dispensing event from the dispensing queue for processing. Some of the processes that may be performed on the dispensing event may include, for exemplary purposed only, patient and provider identification, model-based and configurable orderable to product mapping, syncing of the ordered medication with pharmacy/product catalogs, identify potential products and dispensable units based on the orderable route and active ingredients and comparability and inventory availability, product and administration calculations, prepare dispensing station specific request for a job scheduling and routing, and the like.

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

BRIEF DESCRIPTION OF THE SEVERAL VIEWS OF THE DRAWINGS

The present invention is described in detail below with reference to the attached drawing figures, wherein.

DETAILED DESCRIPTION

Figure 1:
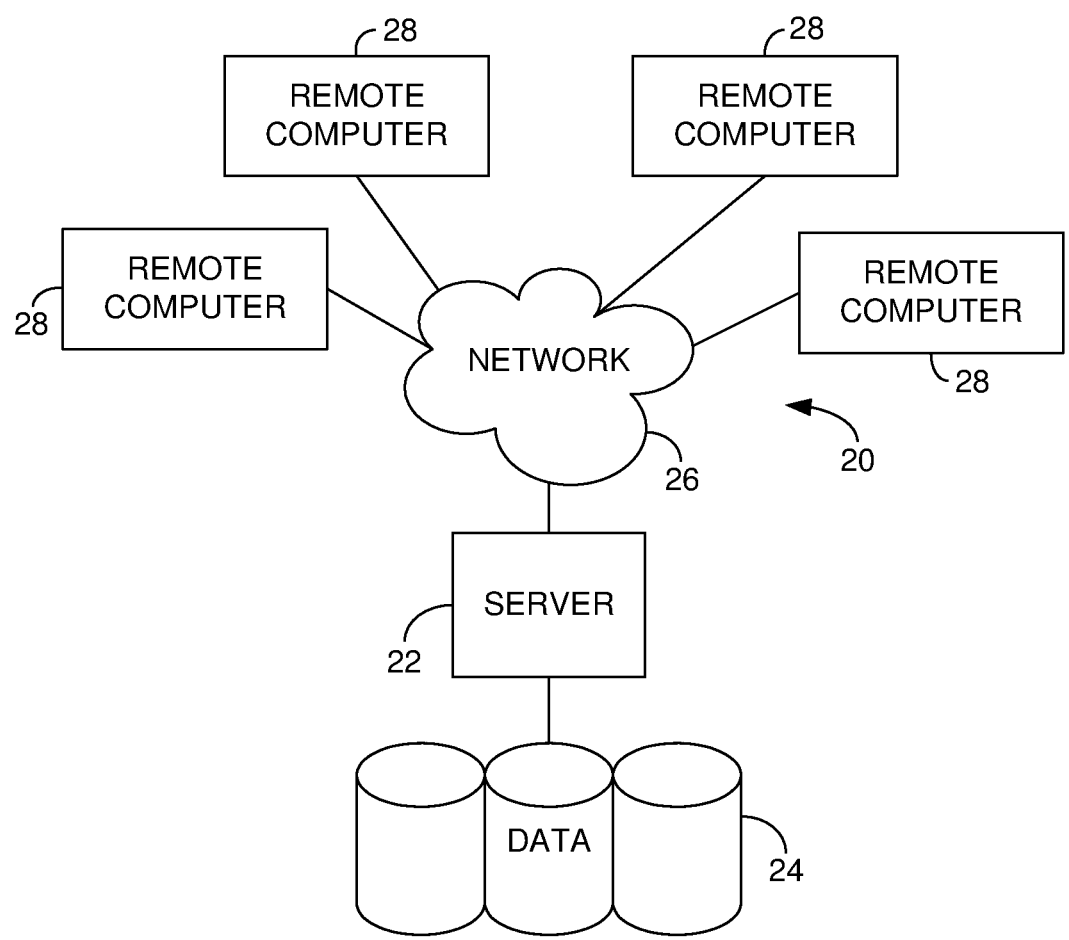
FIG. 1 is a block diagram of an exemplary computing environment suitable for use in implementing the present invention.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different components of methods employed, the terms should not be interpreted as implying any particular order among or between various steps herein disclosed unless and except when the order of individual steps is explicitly described.

Embodiments of the present invention provide for a dispensing system to perform various operations to process an incoming order for a clinician where a medication is to be dispensed from a dispensing station. In embodiments, the information for the order is provided to the system in the form of a dispensing event, either manually by a clinician and/or automatically. The dispensing order may be put in a dispensing queue until the dispensing system can handle the order. Once a particular dispensing event is selected for processing, the system determines which processes are to be performed. These processes may include routing, quantity/dosage calculations, mapping, job scheduling, facility alignment, administration schedule, etc.

In some embodiments, an ordered medication may be mapped to a table, database, list, catalog, etc., to make several determinations, including which medications are available for dispensing, available dosages of those medications, etc. Once the system has determined which medications are compatible with the order, the system may compute dispensed dosages, quantities of tablets/capsules, etc. based on the order. For example, if the order is for 110 mg of Doxycycline Hyclate but available inventory of that drug is 50 mg tablets and capsules and 100 mg tablets and capsules, the system may round 110 mg down to 100 mg, and order either two 50 mg tablets/capsules or one 100 mg capsule for each administration to the patient/individual. The system may also determine which dispensing station has the medication, and if there are multiple, may select one based on location, etc. The system, during processing, may also determine how to route the instructions to the dispensing station, schedule jobs for various dispensing events, and generate an administration schedule for the patient. Once these determinations have been made, the system ensures that other components perform the drug mixing, counting, packaging, labeling, dispensing, marking TOA as dispensed, and the like.

As used herein, a dispensing event is an event that requires processing based on information contained within the dispensing event. In embodiments herein, the dispensing event includes medication/patient information that can be used to cause a dispensing station to dispense of a medication for that patient, based on determinations/computations made by the dispensing system. The dispensing system, as used herein, comprises all components discussed that are used to receive, process, and carry out a dispensing event.

Accordingly, in one aspect, an embodiment of the present invention is directed to one or more computer storage media storing computer-useable instructions that, when used by one or more computing devices, cause the one or more computing devices to perform operations. The operations comprise receiving a dispensing event associated with an order for an individual, and processing the dispensing event. The processing includes mapping a medication listed in the dispensing event to a table that includes a plurality of medications and available dosages, identifying one or more corresponding medications from the table based on the mapping and a dispensable unit for each of the one or more corresponding medications, selecting one of the corresponding medications for administration to the individual, and based on the selected one of the one or more corresponding medications for administration to the individual and the corresponding dispensable unit, computing a quantity of the selected one of the one or more corresponding medications to be dispensed. The operations further comprise instructing a dispensing station to dispense the computed quantity of the selected one of the one or more corresponding medications.

In another embodiment, an aspect is directed to a computer-implemented method for facilitating a dispensing of a medication for administration to an individual based on a dispensing event. The method includes receiving a dispensing event associated with an order for the individual, from the dispensing event, determining an ordered medication and dosage, and identifying medications that correspond to the ordered medication and that are available for dispensing from a dispensing station. Further, the method includes determining a dispensable unit for each of the medications that correspond to the ordered medication, and based, at least, on the determined dispensable unit, selecting a medication that corresponds to the ordered medication. Also, the method includes computing a quantity of the selected one of the one or more medications to be dispensed and instructing, without human intervention, a dispensing station to dispense the computed quantity of the selected one of the one or more medications for administration to the individual.

A further embodiment is directed to a system for facilitating a dispensing of a medication for administration to an individual based on a dispensing event. The system includes a processor and one or more computer storage hardware devices storing computer-usable instructions that, when used by the processor, cause the processor to perform various operations. These operations include, from the dispensing event, determining an ordered medication and dosage, identifying medications that correspond to the ordered medication, that have an associated dispensable unit less than the dosage, and that are available for dispensing from one of a plurality of dispensing stations that is capable of communicating with the system. The operations further includes determining a dispensable unit for each of the medications that correspond to the ordered medication, based, at least, on the determined dispensable unit, selecting a medication that corresponds to the ordered medication for administration to the individual, and computing a quantity and dosage of the selected one of the one or more medications to be dispensed. Even more, the operations includes automatically and without human intervention communicating an instruction to one of the plurality of dispensing stations to dispense the computed quantity of the selected one of the one or more medications for administration to the individual, and receiving an acknowledgment that the computed quantity of the selected one of the one or more medications has been dispensed.

Referring now to the drawings in general, and initially to FIG. 1 in particular, an exemplary computing system environment, for instance, a medical information computing system, on which embodiments of the present invention may be implemented is illustrated and designated generally as reference numeral 20. It will be understood and appreciated by those of ordinary skill in the art that the illustrated medical information computing system environment 20 is merely an example of one suitable computing environment and is not intended to suggest any limitation as to the scope of use or functionality of the invention. Neither should the medical information computing system environment 20 be interpreted as having any dependency or requirement relating to any single component or combination of components illustrated therein.

The present invention may be operational with numerous other general purpose or special purpose computing system environments or configurations. Examples of well-known computing systems, environments, and/or configurations that may be suitable for use with the present invention include, by way of example only, personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

The present invention may be described in the general context of computer-executable instructions, such as program modules, being executed by a computer. Generally, program modules include, but are not limited to, routines, programs, objects, components, and data structures that perform particular tasks or implement particular abstract data types. The present invention may also be practiced in distributed computing environments where tasks are performed by remote processing devices that are linked through a communications network. In a distributed computing environment, program modules may be located in local and/or remote computer storage media including, by way of example only, memory storage devices.

With continued reference to FIG. 1, the exemplary medical information computing system environment 20 includes a general purpose computing device in the form of a server 22. Components of the server 22 may include, without limitation, a processing unit, internal system memory, and a suitable system bus for coupling various system components, including database cluster 24, with the server 22. The system bus may be any of several types of bus structures, including a memory bus or memory controller, a peripheral bus, and a local bus, using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The server 22 typically includes, or has access to, a variety of computer readable media, for instance, database cluster 24. Computer readable media can be any available media that may be accessed by server 22, and includes volatile and nonvolatile media, as well as removable and non-removable media. By way of example, and not limitation, computer readable media may include computer storage media and communication media. Computer storage media may include, without limitation, volatile and nonvolatile media, as well as removable and nonremovable media implemented in any method or technology for storage of information, such as computer readable instructions, data structures, program modules, or other data. In this regard, computer storage media may include, but is not limited to, RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the server 22. Communication media typically embodies computer readable instructions, data structures, program modules, or other data in a modulated data signal, such as a carrier wave or other transport mechanism, and may include any information delivery media. As used herein, the term "modulated data signal" refers to a signal that has one or more of its attributes set or changed in such a manner as to encode information in the signal. By way of example, and not limitation, communication media includes wired media such as a wired network or direct-wired connection, and wireless media such as acoustic, RF, infrared, and other wireless media. Combinations of any of the above also may be included within the scope of computer readable media.

The computer storage media discussed above and illustrated in FIG. 1, including database cluster 24, provide storage of computer readable instructions, data structures, program modules, and other data for the server 22.

The server 22 may operate in a computer network 26 using logical connections to one or more remote computers 28. Remote computers 28 may be located at a variety of locations in a medical or research environment, for example, but not limited to, clinical laboratories, hospitals and other inpatient settings, veterinary environments, ambulatory settings, medical billing and financial offices, hospital administration settings, home health care environments, and clinicians' offices. Clinicians may include, but are not limited to, a treating physician or physicians, specialists such as surgeons, radiologists, cardiologists, and oncologists, emergency medical technicians, physicians' assistants, nurse practitioners, nurses, nurses' aides, pharmacists, dieticians, microbiologists, laboratory experts, genetic counselors, researchers, veterinarians, students, and the like. The remote computers 28 may also be physically located in non-traditional medical care environments so that the entire health care community may be capable of integration on the network. The remote computers 28 may be personal computers, servers, routers, network PCs, peer devices, other common network nodes, or the like, and may include some or all of the components described above in relation to the server 22. The devices can be personal digital assistants or other like devices.

Exemplary computer networks 26 may include, without limitation, local area networks (LANs) and/or wide area networks (WANs). Such networking environments are commonplace in offices, enterprise-wide computer networks, intranets, and the Internet. When utilized in a WAN networking environment, the server 22 may include a modem or other means for establishing communications over the WAN, such as the Internet. In a networked environment, program modules or portions thereof may be stored in the server 22, in the database cluster 24, or on any of the remote computers 28. For example, and not by way of limitation, various application programs may reside on the memory associated with any one or more of the remote computers 28. It will be appreciated by those of ordinary skill in the art that the network connections shown are exemplary and other means of establishing a communications link between the computers (e.g., server 22 and remote computers 28) may be utilized.

In operation, a user may enter commands and information into the server 22 or convey the commands and information to the server 22 via one or more of the remote computers 28 through input devices, such as a keyboard, a pointing device (commonly referred to as a mouse), a trackball, or a touch pad. Other input devices may include, without limitation, microphones, satellite dishes, scanners, or the like. Commands and information may also be sent directly from a remote healthcare device to the server 22. In addition to a monitor, the server 22 and/or remote computers 28 may include other peripheral output devices, such as speakers and a printer.

Although many other internal components of the server 22 and the remote computers 28 are not shown, those of ordinary skill in the art will appreciate that such components and their interconnection are well known. Accordingly, additional details concerning the internal construction of the server 22 and the remote computers 28 are not further disclosed herein.

Figure 2:
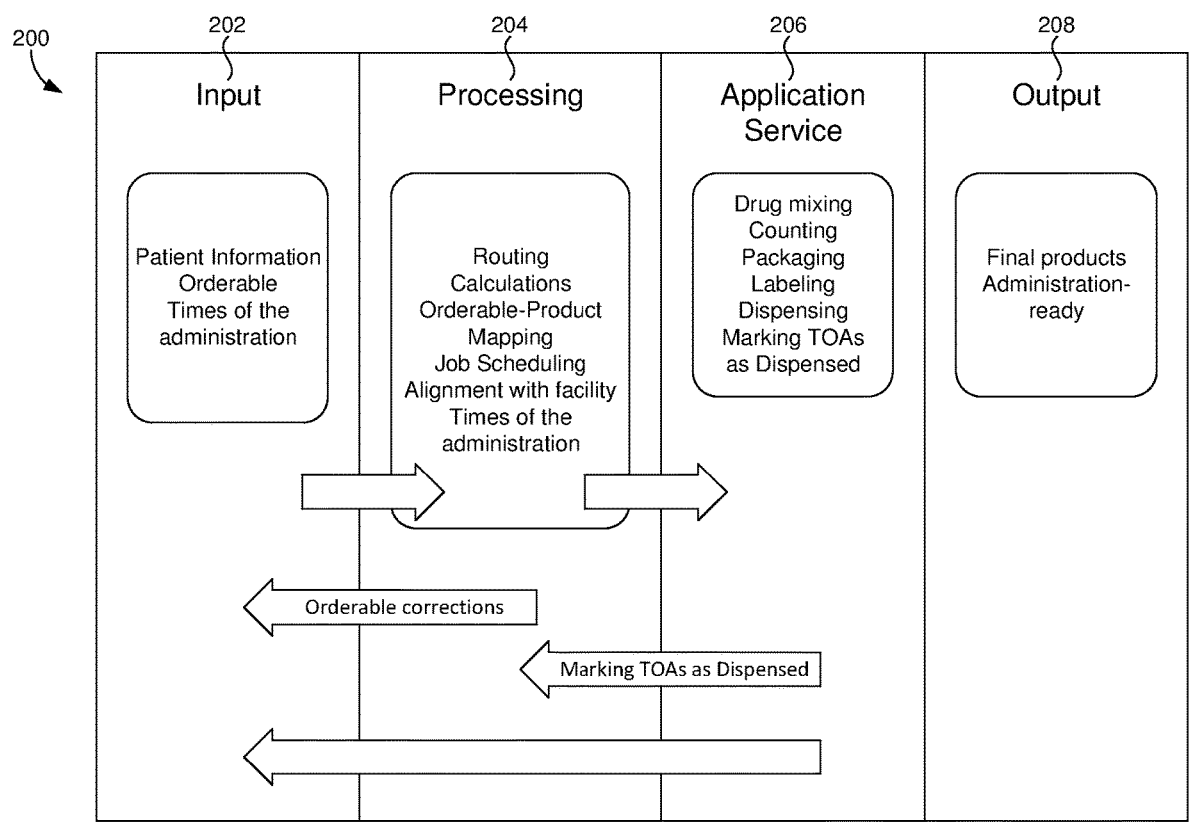
FIG. 2 is a flow diagram of a process for instructing a medication from a dispensing station based on a dispensing event, in accordance with an embodiment of the present invention.

Turning now to FIG. 2, a flow diagram 200 is depicted of a process for instructing a medication from a dispensing station based on a dispensing event, in accordance with an embodiment of the present invention. As illustrated, the input block 202 refers to information that is input by a user, such as a clinician, into the system. This information may be used to generate a dispensing event. In an embodiment, the information that a user may input into the system may include patient identification information, open times of administrations (TOAs), orderable start and stop time, route of administration, pharmacy manufacturing window, facility administration schedule, duration of the therapy, inventory products, patient medication supply, and the like. Processing block 204 represents the various processing operations performed by the system. Some of these processing operations include patient and provider identification, model-based and configurable orderable to product mapping, syncing of the ordered medication with pharmacy/product catalogs, identify potential products and dispensable units based on the orderable route and active ingredients and comparability and inventory availability, product and administration calculations, prepare dispensing station specific request for a job scheduling and routing, and the like.

In one instance, a mapping function is performed by the processing block 204 to compare the ordered medication to medications available by a pharmacy or the dispensing stations. This allows the system to selectively and intelligently choose one or more medications that could be filled for the order associated with the dispensing event. The mapping may include, for example, a lookup table comprising lists of medications, dosages, and a current availability status for each. The lookup table may be dynamically updated to represent the medications available in each dispensing station at any given time. In addition to availability, the system may be capable of determining compatibility matches for the ordered medication. For example, any given medication may have several options that each match the ordered medication, as a medication may be branded by multiple companies, may be provided in different dosages (dispensable units), etc. As such, the result or output of the mapping could be a list of several options that are compatible with the ordered medication.

Once the list is generated of potential options that correspond to the ordered medication, the processing block 204 may perform various calculations to determine which product to select for the order. These calculations could include, for example, administration calculations, as one option on the list may be a higher dose than that specified in the order. In that case, that medication that is at a higher dosage would not be selected by the system, as the system would not, in embodiments, provide a medication to a patient that is at a higher dosage than what is provided for in the order, unless the ordering clinician is consulted. Alternatively, if a medication on the list is a lower dosage than that in the order, the system could determine a quantity of pills, capsules, etc., that would need to be provided to the patient to be equivalent (or as close as possible) to the ordered dosage. Examples provided below will further describe the calculations that the system may make.

In addition, processing block 204 may select a dispensing station from which the medication will be dispensed for each dispensing event. In embodiments, multiple dispensing stations may be available in a hospital or other medical building, and as such, a decision may be made as to which dispensing station to use for each dispensing event. This decision made by the system could be based on one or more factors, including location, inventory availability of a certain medication, etc. To discuss dispensing stations in more detail, FIG. 7 is provided, which illustrates an exemplary scene 700 associated with a clinician 704 retrieving medications from a medication dispensing station 702 suitable to implement embodiments of the present invention.

Figure 7:
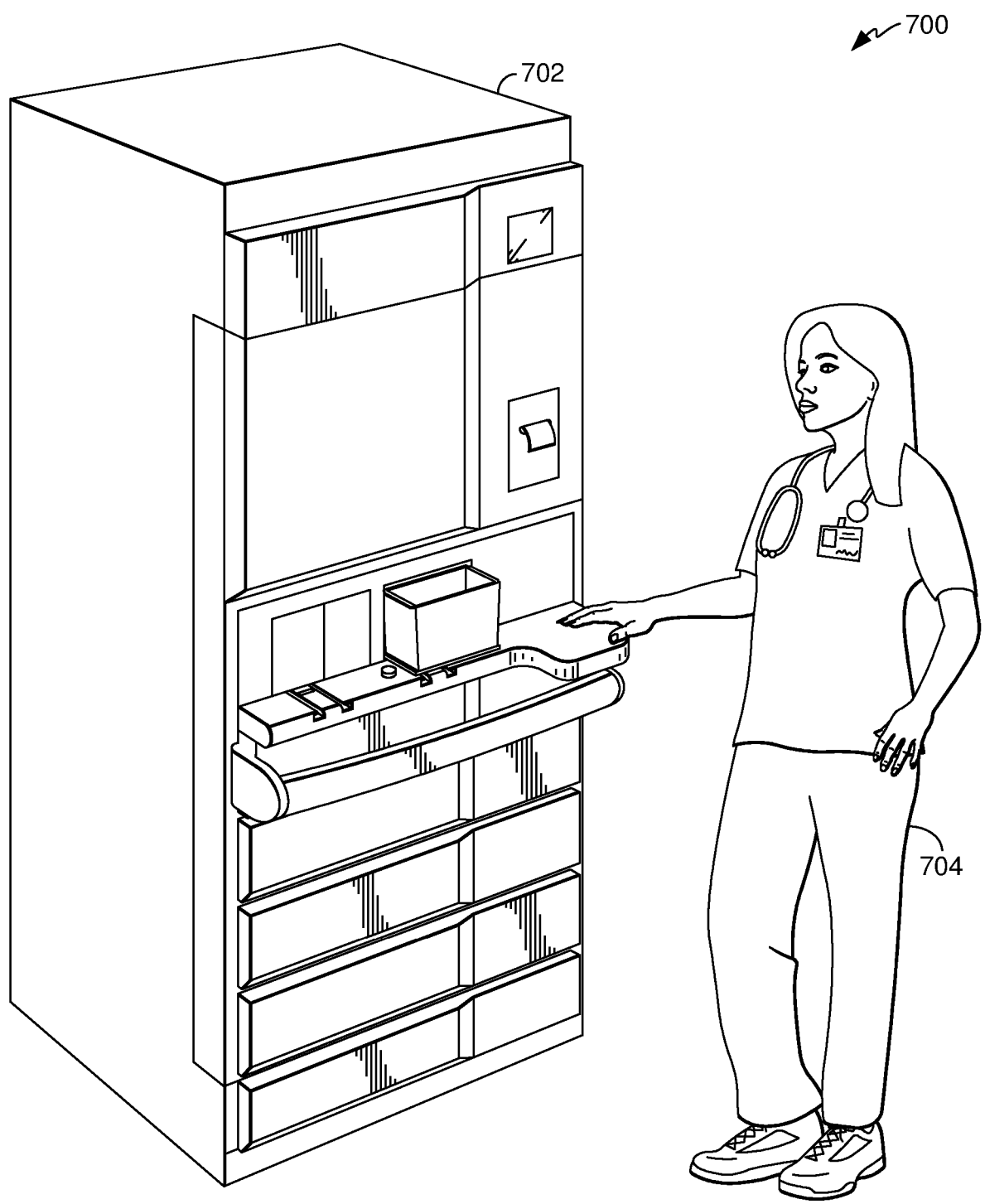
FIG. 7 depicts an exemplary scene associated with a clinician retrieving medications from a medication dispensing station suitable to implement embodiments of the present invention.

In particular, FIG. 7 depicts a clinician 704 interacting with a medication dispensing station 702. The medication dispensing station 702 is multi-patient oriented medical device that contains medications that are associated with one or more patients. The medication dispensing station 702 generally contains medications for patients located in proximity to an area surrounding the medication dispensing station 702 (e.g., patients in the same hospital wing as the medication dispensing station 702).

The medication dispensing station 702 generally contains multiple compartments. Each compartment is stocked with a certain medication. Typically, when a clinician 704 wishes to begin the medication-administration process for a patient, the clinician 704 interacts with a computer system associated with the medication dispensing station 702 to access the medication orders for that patient (for example, the computer system may access medication orders from an electronic medical record). The computer system determines the location of the compartment that contains an ordered medication and automatically opens that compartment. Upon withdrawal of the medication by the clinician 704, the medication is associated with the patient. This process is repeated for each ordered medication. In one aspect, the clinician 704 may provide feedback to the computer system to verify that a specific medication has been removed from the medication dispensing station 702. In another aspect, the medication dispensing station 702 automatically detects when a medication(s) has been retrieved for a patient. However, in embodiments provided herein, the system, as described, may automatically determine which dispensing station has a particular medication that correlates with the ordered medication from a dispensing event, as well as make dosage and administration calculations, as further described herein.

Returning to FIG. 2, application services block 206 is responsible for drug mixing, counting (e.g., pills), packaging, labeling, dispensing, and marking times of administration as dispensed. Application services block 206 ensures that each of these tasks has been properly completed. Output block 208 of FIG. 2 ensures that the medication is output from the correct dispensing station, has proper labeling, and that it is ready for administration by a clinician.

Figure 3:
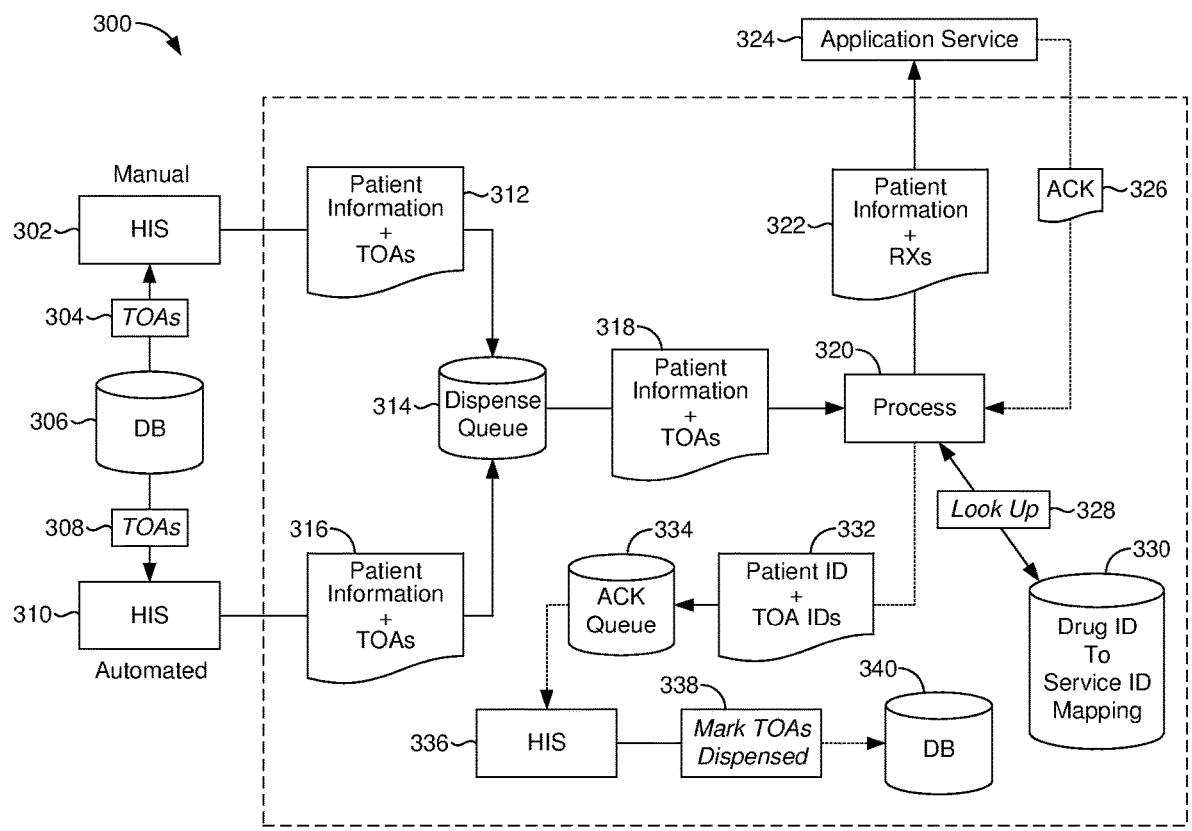
FIG. 3 is a block diagram for facilitating a dispensing of a medication from a dispensing station based on a dispensing event, in accordance with an embodiment of the present invention.

FIG. 3 is a block diagram 300 for facilitating a dispensing of a medication from a dispensing station based on a dispensing event, in accordance with an embodiment of the present invention. Initially, a clinician may enter an order into the system, such as manually through the health information system (HIS) 302 or it may be entered automatically through HIS 310. Whether entered manually or automatically, time of administration (TOA) information (items 304 and 308) may be pulled from database 306 to be used in the dispensing event. Blocks 312 and 316 indicate that at least patient information and TOA information are passed to the dispense queue 314. In embodiments, this information is stored as a dispensing event, such that dispensing queue 314 stores one or more dispensing events that are waiting for processing. Once the system has capacity to process a dispensing event, it pulls from the dispense queue 314 so that the patient information and TOA information (e.g., dispensing event) is passed to the process block 320. Process block 320 operates as described above with respect to processing block 204 of FIG. 2. For example, as shown in FIG. 3, process block 320 may perform a mapping function 330 to identify medications that are available (e.g., in inventory) and that are compatible (e.g., an exact match or similar) with the ordered medication. This mapping could include, for instance, a lookup table, lists, product catalogs, etc. Process block 320 also communicates with application service 324, which performs functions described above with respect to application service block 206 of FIG. 2. For instance, patient information and a list of prescriptions identified from, for example, the mapping function, may be sent to application service 324 so that the functions described in FIG. 2 can be performed. An acknowledgement 326 may then be sent from application services 324 to process block 320 confirming that application services 324 has completed its tasks.

Once process block 320 has completed the mapping function and any other tasks to make a determination as to which medication is to be dispensed and an administration schedule for that medication, process block 320 may send the patient ID and TOA IDs 332, along with all other information that has been computed and determined by process block 320, to an acknowledgement queue 334. The acknowledgement queue 334 stores this information, until it is ready to send to HIS 336 so that the medication and administration information can be routed to the dispensing station. HIS 336 then sends instructions that the medication can be marked as being dispensed, shown by block 338. This information may be stored in database 340.

Figure 4:
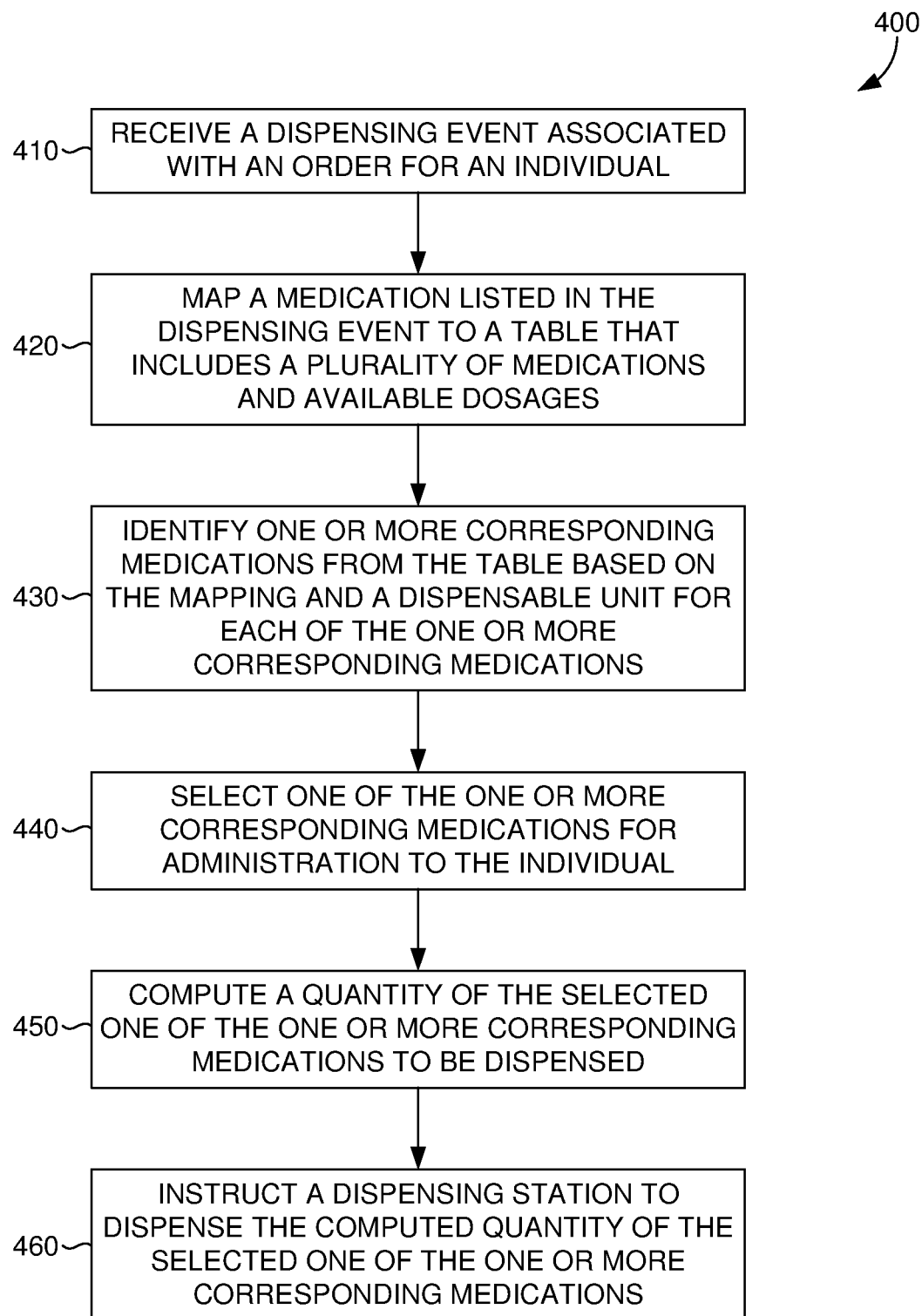
FIG. 4 is a flow diagram of a method for facilitating a dispensing of a medication from a dispensing station based on a dispensing event, in accordance with an embodiment of the present invention.

Referring to FIG. 4, a flow diagram is shown of a method 400 for facilitating a dispensing of a medication from a dispensing station based on a dispensing event, in accordance with an embodiment of the present invention. Initially, a dispensing event associated with an order for an individual is received at block 410. A dispensing event is associated with an order for a medication for a particular patient. Each dispensing event may include information such as, for exemplary purposes only, patient identification information, open TOAs, orderable start and stop time, route of administration, pharmacy manufacturing window, facility administration schedule, duration of the therapy, inventory products, patient medication supply, and the like. At block 420, a medication listed in the dispensing event is mapped to a table that includes a plurality of medications and available dosages. This information can be used by the system to identify a single medication to dispense for that particular dispensing event. At block 430, one or more corresponding medications from the table are identified based on the mapping and a dispensable unit for each medication. As an example, it may be determined that at least one of the plurality of medications in the table may have an available dosage that is greater than a dosage specified in the dispensing event. In this instance, that particular medication may not be selected as a potential mediation for being dispensed and administered to a patient. In one instance, it may be determined that at least one of the identified medications from the table is out of stock in a particular dispensing station. In this case, that particular dispensing station may not be utilized for the dispensing event.

At block 440, the system selects one of the medications for administration to the patient. In addition to selecting one of the medications, the system may also identify a dispensing station in which the selected medication resides. At block 450, a quantity of the selected medication to be dispensed is computed, such that the dosage of the medication to be dispensed matches the ordered dosage of the medication. As will be detailed in the examples provided herein, the dispensed dosage may be less than the ordered dosage, which could be based on the available units of the medication. Computing the quantity may comprise comparing a dosage indicated in the dispensing event to the corresponding dispensable unit of the selected medication, and determining how many dispensable units are to be dispensed such that the dosage of the selected medication is not greater than the dosage indicated in the dispensing event. In some embodiments, an administration schedule may be determined for the patient based on the computed quantity of the selected medication to be dispensed. At block 460, a dispensing station is instructed to dispense the computed quantity of the selected medication. Once instructed, the dispensing station may dispense the computed quantity of the selected medication. In some embodiments, an acknowledgement may be received indicating that the computed quantity of the medication has been dispensed from the dispensing station.

Figure 5:
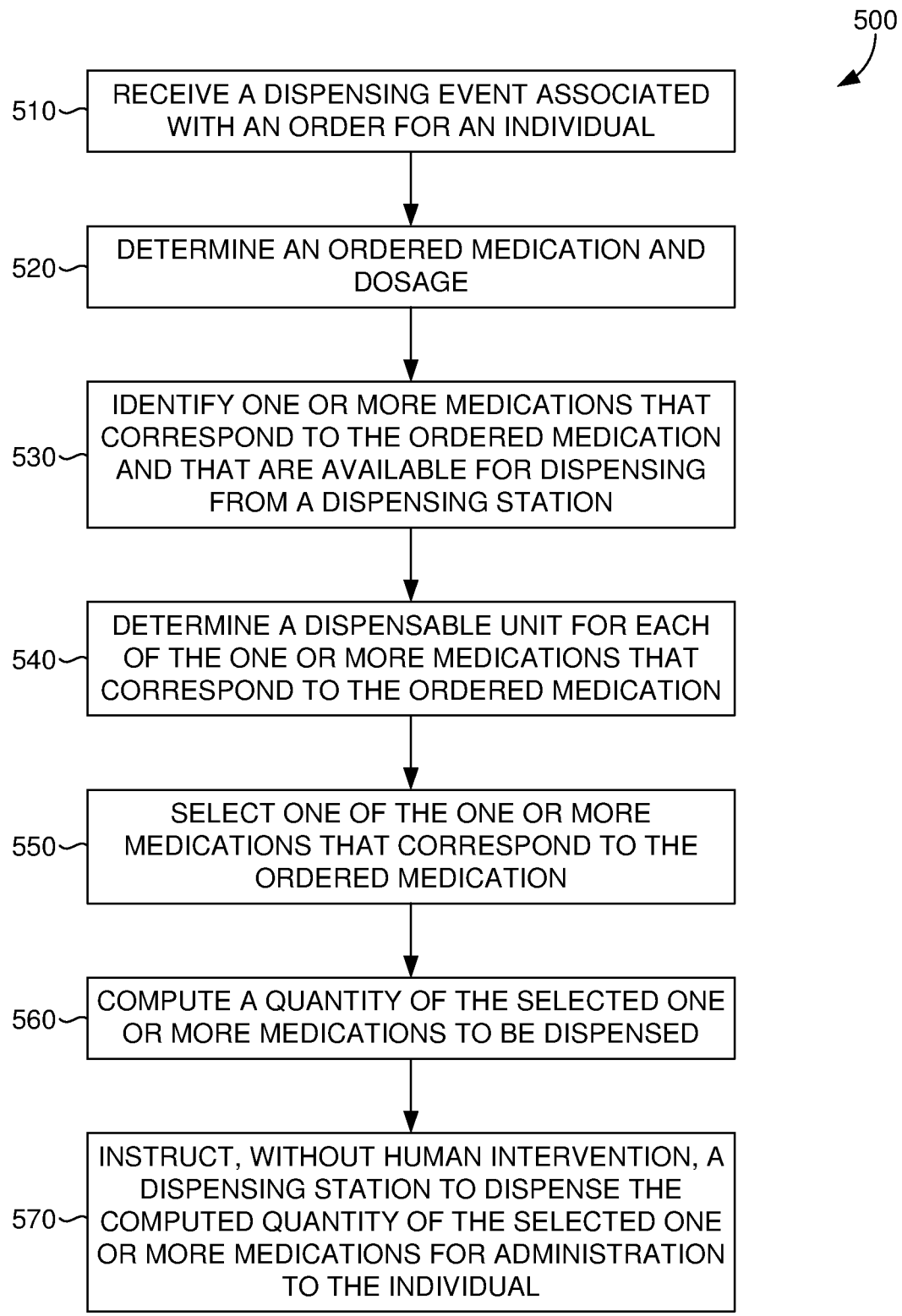
FIG. 5 is a flow diagram of another method for facilitating a dispensing of a medication from a dispensing station based on a dispensing event, in accordance with an embodiment of the present invention.

Turning to FIG. 5, a flow diagram is depicted of another method 500 for facilitating a dispensing of a medication from a dispensing station based on a dispensing event, in accordance with an embodiment of the present invention. At block 510, a dispensing event associated with an order for a patient is received. An ordered medication and ordered dosage are determined from the dispensing event, shown at block 520. At block 530, one or more medications that correspond to the ordered medication and that are available for dispensing from a dispensing station are identified. In embodiments, a medication that corresponds to the ordered medication may be an exact match, or may be a clinically effective or appropriate substitution. It could be the same chemical composition but a different brand name than that in the dispensable event. Or it could be a clinically acceptable replacement that is known and/or approved to be used for the same purpose. Alternatively, it could be the same drug, but could include inactive ingredients that differ from the ordered medication.

At block 540, a dispensable unit for each of the identified medications that corresponds to the ordered medication is determined. A dispensable unit, as used herein, refers to the strength of a drug (e.g. 500 mg capsule, 250 mg/5 mL suspension), or the dosage of a single unit. A tablet of ibuprofen, for instance, may be 200 mg, 500 mg, 1000 mg, etc. At block 550, one of the medications that correspond to the ordered medication is selected. This selection could be based on one or more factors, such as the available dosage, inventory availability in various dispensing stations, etc. Once the medication that is to be dispensed is selected, a quantity of the selected medication to be dispensed is computed, shown at block 560. Using the above example, if the ordered medication is for 400 mg of ibuprofen in a single administration to a patient, the system may not select the 500 mg tablet, but may instead select two 200 mg tablets for administration, as that would be equivalent to a 400 mg dose. Thus, the system would compute that two tablets should be administered to the patient for a single dosage. Additionally, if multiple dispensing stations have the selected medication available, the system may identify one of the dispensing stations for the particular dispensing event based, at least, on the identified dispensing station having the computed quantity of the selected medication available, or a location of the dispensing station in relation to the clinician, the individual, etc. At block 570, the system instructs, without human intervention, a dispensing station to dispense the computed quantity of the selected medication for administration to the patient. In an embodiment, instructing the dispensing station may comprise routing the administration instructions to the dispensing station according to the routing instructions.

In some embodiments, an administration schedule is generated based on the computed quantity of the selected medication, a dosage provided, etc. The administration schedule generated could differ from that in the dispensing event, such as if the ordered dosage is different from the dosage determined by the system. Once the system has computed quantities, dosages, administration schedules, etc., it may generate administration instructions for the administration of the selected medication, and may further generate routing instructions for communicating the administration instructions to the dispensing station. The routing instructions may be used not only for communicating administration instructions to the dispensing station, but also for communicating dispensing instructions to the dispensing station, such as that it is to dispense the medication at a certain time, for a certain patient, etc.

Figure 6:
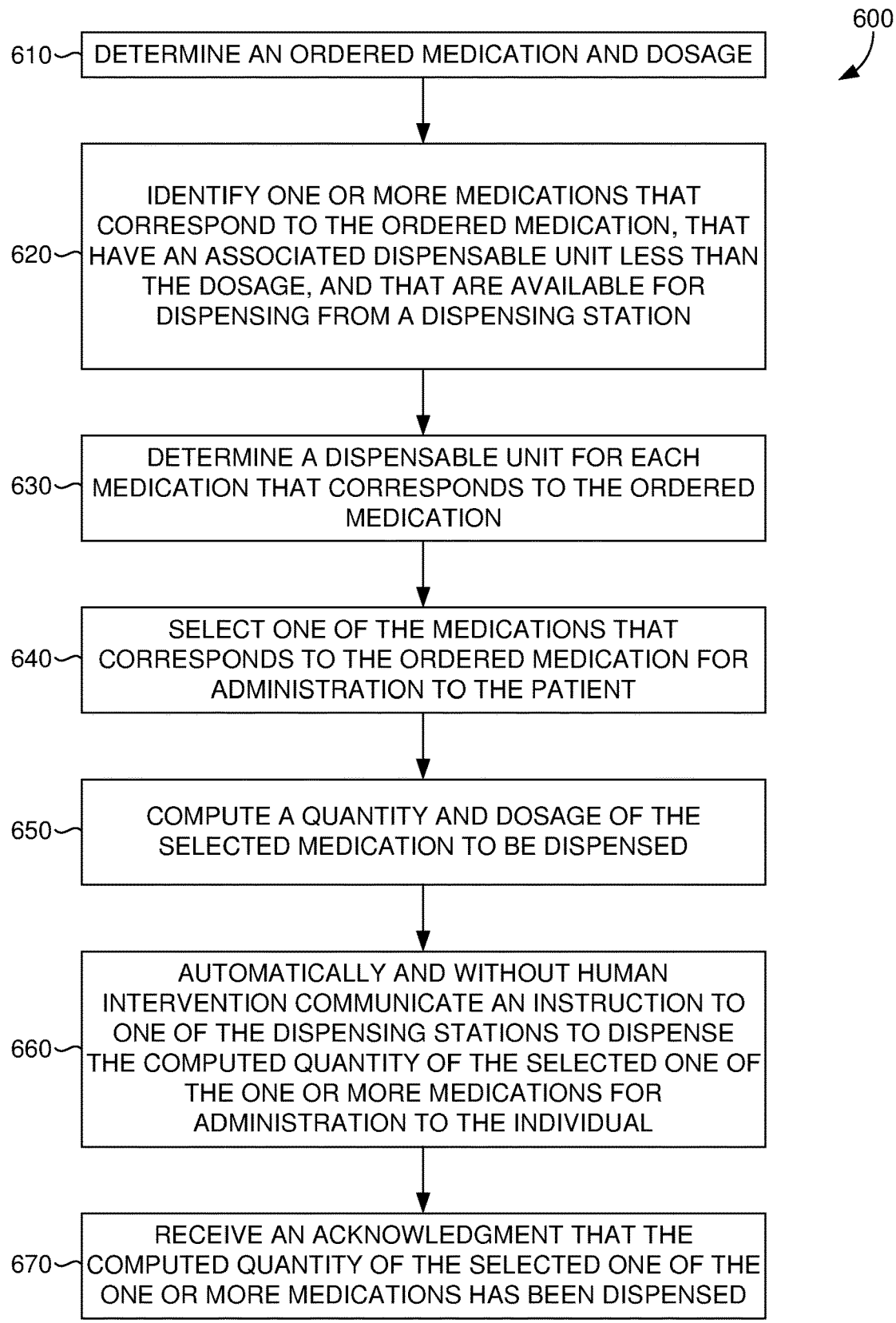
FIG. 6 is a flow diagram of another method for facilitating a dispensing of a medication from a dispensing station based on a dispensing event, in accordance with an embodiment of the present invention.

FIG. 6 is a flow diagram of another method 600 for facilitating a dispensing of a medication from a dispensing station based on a dispensing event, in accordance with an embodiment of the present invention. At block 610, an ordered medication and dosage are determined, such as from a dispensing event that includes the information needed for the system to instruct a dispensing station to dispense a medication. At block 620, one or more medications that correspond to the ordered medication are identified. In embodiments, these medications identified have an associated dispensable unit less than the ordered dosage, and are available for dispensing from one of a plurality of dispensing stations that can communicate with the system.

At block 630, a dispensable unit for each of the one or more medications is determined. The system selects one of these medications for administration to the individual. At block 640, one of the medications that corresponds to the ordered medication is selected. Once the medication to be dispensed has been selected by the system, an administration schedule may be determined, which could be based on the computed quantity of the medication, dosage, etc. At block 650, a quantity and dosage of the selected medication to be dispensed is computed. Automatically and without human intervention, an instruction is communicated to the dispensing station to dispense the computed quantity of the selected medication for administration to the individual, shown at block 660. In some instances, the system identifies a dispensing station from a plurality of dispensing stations based, at least, on the dispensing station having the computed quantity of the selected medication available at the correct dosage. At block 670, an acknowledgment is received that the computed quantity of the selected medication has been dispensed. It is noted that the dispensing system may include the dispensing stations, and as such, the dispensing system described herein may actually dispense the medication. Therefore, additionally, the dispensing station may receiving instructions for dispensing the medication, and may take the actual, physical steps needed to dispense the medication.

EXAMPLES

Example 1

The input provided in a dispensable event of this Example 1 includes the following:
Time of the request submission
Orderable start and stop time
Orderable—Doxycycline Hyclate 110 mg BID for 7 days.
Route of the administration—oral
TOA—BID (twice a day).
Pharmacy Manufacturing Window—24 hours, 9 am.
Facility administration schedule: 8 am, 11 am, 4 pm, 7 pm, 10 pm,
Duration of the therapy—7 days The system then maps the ordered medication to a table, list, catalog, etc., to determine which products/medications are available in inventory that correspond to the ordered medication. Here, the inventory products include the following:
Doxycycline Hyclate—50 mg capsules—in stock
Doxycycline Hyclate—100 mg capsules—1 tablet in inventory
Doxycycline Hyclate—50 mg tablets—in stock
Doxycycline Hyclate—100 mg tablets—out of stock
Vibramycin—50 mg capsules—in stock
Vibramycin—100 mg capsules—out of stock
Periostat—20 mg—1000 tablets in inventory
Periostat—100 mg—2 tablets in inventory
Vibramycin—20 mg tablets—out of stock
Vibramycin—100 mg tablets—out of stock The following table lists a subset of the NDCs and labelers of Doxycycline Hyclate:

| NDC | Trade Name | Labeler Name |
| --- | --- | --- |
| 54569-0118 | Doxycycline Hyclate | A-S Medication Solutions LLC |
| 54569-0147 | Doxycycline Hyclate | A-S Medication Solutions LLC |
| 00591-5535 | Doxycycline Hyclate | Actavis Pharma, Inc. |
| 00591-5553 | Doxycycline Hyclate | Actavis Pharma, Inc. |
| 33261-0151 | Doxycycline Hyclate | Aidarex Pharmaceuticals LLC |
| 33261-0888 | Doxycycline Hyclate | Aidarex Pharmaceuticals LLC |
| 33261-0899 | Doxycycline Hyclate | Aidarex Pharmaceuticals LLC |
| 60687-0118 | Doxycycline Hyclate | American Health Packaging |
| 68084-0939 | Doxycycline Hyclate | American Health Packaging |
| 15338-0100 | Doxycycline Hyclate | Apace Packaging LLC |
| 53401-0100 | Doxycycline Hyclate | Aphena Pharma Solutions (Formerly TestPak) |
| 42852-0002 | Doxycycline Hyclate | Apothecary Shop Wholesale Inc. |
| 69189-0391 | Doxycycline Hyclate | Avera McKennan Hospital |

Once all of the information above has been gathered, the system begins to perform various processing functions. Initially, the system rounds the ordered dosage to 100 mg, as this particular medication is not available in 10 mg increments. Doxycycline Hyclate 50 mg capsules are chosen by the system and considered for calculations. Because of inventory constrains, as shown above, the system determines the smallest dispensable unit as 50 mg, such that 2 capsules of the 50 mg medication will be dispensed to fulfill a single 100 mg dose. In this case, capsules and tablets are interchangeable, but may not be in other cases. Due to the manufacturing window settings as 24 hours at 9 am, the system determines an administration schedule of 8:00 AM and 5:00 PM for this particular dispensable event.

After processing has taken place, the dispensing station is given instructions to package together 2 capsules of 50 mg Doxycycline Hyclate and attach an appropriate instruction that the patient is to take two capsules at each time of administration (twice a day). These two capsules will be packaged together for the single dose administration with the attached label with instructions.

Example 2

The input provided in a dispensable event of this Example 1 includes the following:
Time of the request submission.
Orderable start and stop time
Orderable—½ NS 1000 ML+10 mEq KCl IV at 100 mL/hr
Route of the administration—intravenous.
TOA—Continues infusion.
Pharmacy Manufacturing Window—24 hours, 9 am.
Facility administration schedule: 8 am, 11 am, 4 pm, 7 pm, 10 pm,
Duration of the therapy—open order, no stop date.

The system then maps the ordered medication to a table, list, catalog, etc., to determine which products/medications are available in inventory that correspond to the ordered medication. Here, the inventory products include the following:
Base Product is Normal Saline 0.45% (½NS)—1000 mL bags, NDC XYZZ
Base Product is Normal Saline 0.45% (½NS)—500 mL bags, NDC XXYZ
Additive product 20 ml vial of the KCl is configured with a concentration of 5 mEq/mL NDC XYZA
Additive product 2 ml vial of the KCl is configured with a concentration of 2 mEq/mL NDC XYZB Once all of the information above has been gathered, the system begins to perform various processing functions. The system determines the product or combination of products for the given orderable it required to identify a base solution and additive to fulfill this order. The appropriate dispensable unit will be 1000 ml (bag). The system will also determine 3000 mls=3 L of the total volume of the IV solution should to be dispensed, so that with rate of 100 ml/hour, it will last until the next dispensing window. In addition, there are 3 labels (with the special instructions that bags should be changed every 10 hours) that will be printed and attached to each of the final products by the machine. Each bag of ½NS L will contain 2 ml of the additive that was injected by the machine so that the patient will receive a consistent dose of the 10 mEq/L.

The internal IV dispense calculations performed by the system are as follows: For this example, the smallest dispensable unit is 1 bag=1 L=1000 ml. The assumption is that the pharmacy manufacturing window is 24 hours. The order is placed for 100 mL/Hour for 24 hours. The system calculates 2400 mL for 24 hours. The product is Normal Saline 0.45% (½NS) in 1000 mL bags (as configured for the product). The system calculates that there will be 2.4 bags for 24 hours, which is rounded to 3 bags, as bags only can be dispensed in whole numbers. The system creates 3 occurrences/administrations. Each bag lasts 10 hours (based on the rate and size of the bag, using 1 L=1000 ml bags), so the TOA would be every 10 hours. e.g. 11 am, 9 pm, 7 am.

For the additives: 20 ml vial of the KCl is configured with a concentration of 5 mEq/mL. The order is placed for 10 mEq/L of an additive. One bag of base is 1000 mL (1L), as noted above. The system calculates that there will be 10 mEq of additive in each bag, and that the required 10 mEq of additive is equivalent to 2 mL. The additive product is configured with 20 mL in each vial, such that 2 mL is 0.1 vials. Depending upon whether the compounding machine can extract multiple times from the same vial, 0.1 vial may be rounded to 1 vial. The logic will be adjusted since vials are not to be shared across occurrences/administrations. For our example, since there are 3 occurrences, we calculate that there will be 3 vials.

From the foregoing, it will be seen that this invention is one well adapted to attain all the ends and objects set forth above, together with other advantages which are obvious and inherent to the system and method. It will be understood that certain features and subcombinations are of utility and may be employed without reference to other features and subcombinations. This is contemplated and within the scope of the claims.

What is claimed is:

1. A system for facilitating a dispensing of a medication for administration to an individual based on a dispensing event, the system comprising:
   a processor; and
   one or more computer storage hardware devices storing computer-usable instructions that, when used by the processor, cause the processor to:
      receive the dispensing event associated with an order for the individual, the order comprising an ordered medication and a total ordered dosage of the ordered medication;
      process the dispensing event received, the processing comprising:
         mapping the ordered medication listed in the dispensing event to a table that includes a plurality of available medications that have an associated dispensable unit for each available medication, the associated dispensable unit being a unit of the available medication to formulate a dosage, the table including the plurality of available medications corresponding to a plurality of dispensing stations located at different physical locations;
         identify one or more medications that correspond to the order from the table based on the mapping;
         determine the associated dispensable unit for each of the one or more medications;
         based on availability of the one or more medications, select a first medication of the one or more medications identified;
         select a dispensing station of the plurality of dispensing stations based on the associated dispensable unit of the first medication; and
      automatically and without human intervention, communicate an instruction to the dispensing station to dispense the first total dosage of the first medication.

2. The system of claim 1, wherein the processor is further caused to determine an administration schedule based on the first total dosage.

3. The system of claim 1, wherein the processor is further caused to receive an acknowledgment that the first total dosage of the first medication has been dispensed by the dispensing station having the first total dosage.

4. One or more non-transitory computer storage media storing computer-useable instructions that, when used by one or more computing devices, cause the one or more computing devices to perform operations, the operations comprising:
   receiving a dispensing event associated with an order for an individual, the order comprising an ordered medication and a total ordered dosage of the ordered medication;
   processing the dispensing event, the processing comprising:
      (1) mapping the ordered medication listed in the dispensing event to a table that includes a plurality of available medications that have an associated dispensable unit for each available medication, the associated dispensable unit being a unit of the available medication to formulate a dosage, the table including the plurality of available medications corresponding to a plurality of dispensing stations located at different physical locations;
      (2) identifying one or more available medications corresponding to the order from the table based on the mapping;
      (3) determining the associated dispensable unit for each of the one or more available medications;
      (4) selecting a first medication of the one or more available medications based on availability of the one or more available medications; and
      (5) based on the associated dispensable unit of the first medication available for dispensing, selecting a dispensing station of the plurality of dispensing stations; and
   instructing the selected dispensing station to dispense a first total dosage of the first medication.

5. The one or more computer storage media of claim 4, wherein selecting the dispensing station is further based on a time of administration and a compatibility level of the first medication compared to the ordered medication, and wherein the dispensing event comprises patient identification information and ordered medication information.

6. The one or more computer storage media of claim 4, further comprising determining a quantity of the first total dosage to be administered within a period of time, and wherein the table that includes the plurality of available medications further includes times for manufacturing windows for medications that are currently out of stock.

7. The one or more computer storage media of claim 4, further comprising identifying the dispensing station in which the first medication resides.

8. The one or more computer storage media of claim 4, further comprising determining an administration schedule for the individual based on the first total dosage.

9. The one or more computer storage media of claim 4, further comprising based on the instructing, dispensing the first total dosage of the first medication from the dispensing station.

10. The one or more computer storage media of claim 4, receiving an acknowledgment event indicating that the first total dosage has been dispensed from the dispensing station.

11. The one or more computer storage media of claim 4, wherein the first total dosage comprises a first total strength of an active drug for a particular administration to the individual.

12. A computer-implemented method for facilitating a dispensing of a medication for administration to an individual based on a dispensing event, the method comprising:
  receiving the dispensing event associated with an order for the individual, the order comprising an ordered medication and a total ordered dosage of the ordered medication;
  based on the dispensing event, mapping the ordered medication to a table that includes a plurality of available medications that have an associated dispensable unit and an associated dispensing station for each of the plurality of available medications;
  identifying one or more medications that correspond to the ordered medication and the table;
  determine the associated dispensable unit for each of the one or more medications;
  select a first medication of the one or more medications based on availability of the one or more medications; and
  automatically instructing, without human intervention, the associated dispensing station to dispense a first total dosage of the first medication.

13. The method of claim 12, further comprising determining an administration schedule based on the first total dosage.

14. The method of claim 13, wherein the administration schedule is determined based on an ordered administration schedule in the dispensing event.

15. The method of claim 12, further comprising generating administration instructions for the administration of the first medication.

16. The method of claim 15, further comprising generating routing instructions for communicating instruction for the administration to the dispensing station.

17. The method of claim 16, wherein automatically instructing, without human intervention, the dispensing station further comprises routing the instruction for the administration to the dispensing station according to the routing instructions.

18. The method of claim 12, wherein selecting the first medication further comprises analyzing inventory availability information and comparability information of the one or more medications and the ordered medication.

* * * * *